US012758162B2

(12) United States Patent
Butani et al.

(10) Patent No.: US 12,758,162 B2
(45) Date of Patent: Oct. 13, 2026

(54) SYSTEM AND METHOD FOR CABINET X-RAY SYSTEMS WITH 3-D OPTICAL IMAGING RECONSTRUCTION

(71) Applicant: KUB TECHNOLOGIES, INC., Stratford, CT (US)

(72) Inventors: Vikram Butani, Fairfield, CT (US); Chester Lowe, Palm Springs, CA (US); Hrituja Babar, Fairfield, CT (US); Jhonah Felipe, Stratford, CT (US); Aditya Ghume, Stratford, CT (US); Mustafa Merchant, Stratford, CT (US); Karla Palma, Stratford, CT (US); Vivek Raut, Stratford, CT (US); Arpit Soni, Fairfield, CT (US); Reshma Sunny, Fairfield, CT (US); Jeet Trivedi, Fairfield, CT (US); Deeksha Khanna, Stratford, CT (US)

(73) Assignee: KUB TECHNOLOGIES, INC., Stratford, CT (US)

( * ) Notice: Subject to any disclaimer, the term of this patent is extended or adjusted under 35 U.S.C. 154(b) by 191 days.

(21) Appl. No.: 18/534,592

(22) Filed: Dec. 9, 2023

(65) Prior Publication Data

US 2025/0114051 A1 Apr. 10, 2025

Related U.S. Application Data

(60) Provisional application No. 63/543,181, filed on Oct. 9, 2023.

(51) Int. Cl.
*A61B 6/02* (2006.01)
*A61B 6/00* (2024.01)
(Continued)

(52) U.S. Cl.
CPC ............ *A61B 6/025* (2013.01); *A61B 6/4208* (2013.01); *A61B 6/4429* (2013.01); *A61B 6/466* (2013.01)

(58) Field of Classification Search
CPC ..... A61B 6/025; A61B 6/4208; A61B 6/4429; A61B 6/466
See application file for complete search history.

(56) References Cited

U.S. PATENT DOCUMENTS 5,023,895 A * 6/1991 McCroskey ......... G01N 23/046 378/177
5,864,146 A * 1/1999 Karellas ................. A61B 6/502 378/191
(Continued)

OTHER PUBLICATIONS

Written Opinion of the International Searching Authority issued Feb. 24, 2025 for application PCT/US2024/059211 (Year: 2025).*
(Continued)

*Primary Examiner* — Blake C Riddick
(74) *Attorney, Agent, or Firm* — Ziegler IP Law Group, LLC.

(57) ABSTRACT

A cabinet x-ray incorporates an x-ray tube, an x-ray detector, and a real-time camera, either High Definition or Standard Resolution, for the production of organic and non-organic images. The computing device receives video data from the real-time camera and the x-ray detector and determines, based on the video data, an overlay of the captured x-ray image with the captured real-time image or display images adjacently i.e. Picture-In-Picture (PIP). The apparatus captures a real-time image simultaneously with the x-ray image allowing a cabinet x-ray unit to attain and optimize images with exact orientation of the 2 images.

10 Claims, 4 Drawing Sheets

SYSTEM AND METHOD FOR CABINET X-RAY SYSTEMS WITH 3-D OPTICAL IMAGING RECONSTRUCTION

DIAGRAMS

FRONT VIEW INTO CABINET
Door Open

(51) Int. Cl.
*A61B 6/42* (2024.01)
*A61B 6/46* (2024.01)

(56) References Cited

U.S. PATENT DOCUMENTS 6,028,910 A * 2/2000 Kirchner .............. G01N 23/044 378/22
6,234,672 B1 * 5/2001 Tomasetti ............ A61B 6/4423 378/114
6,236,712 B1 * 5/2001 Tomasetti ............ A61B 6/4441 378/114
6,256,374 B1 * 7/2001 Tomasetti .............. A61B 6/464 378/98.2
6,363,134 B1 * 3/2002 Suzuki ................... A61B 6/032 378/4
6,827,489 B2 * 12/2004 Nicolas .................... A61B 6/08 378/68
7,412,024 B1 * 8/2008 Yun ........................ A61B 6/484 378/53
11,039,803 B1 * 6/2021 Butani ................. A61B 6/4258
2002/0070365 A1 * 6/2002 Karellas ............... A61B 6/4241 250/581
2002/0090057 A1 * 7/2002 Sykes ...................... H05G 1/02 378/208
2002/0094119 A1 * 7/2002 Sahadevan ............. G16H 30/40 382/132
2004/0076319 A1 * 4/2004 Fauver ............... G01N 15/1468 382/133
2004/0208275 A1 * 10/2004 Adachi ................ G01N 23/046 378/4
2007/0036264 A1 * 2/2007 Beyrard ................... A61B 6/04 378/19
2009/0003519 A1 * 1/2009 Defreitas ............... A61B 6/502 378/37
2009/0238334 A1 * 9/2009 Brahme ............... A61B 6/4092 378/41
2010/0020920 A1 * 1/2010 Mertelmeier .......... A61B 6/025 378/197
2011/0282181 A1 * 11/2011 Wang ................... A61B 5/0095 600/407
2012/0128118 A1 * 5/2012 Graumann ........... A61B 6/4028 378/9
2012/0165654 A1 * 6/2012 Rapoport ............. G01R 33/282 600/431
2014/0249402 A1 * 9/2014 Kimchy .................. G01T 1/161 600/436
2015/0131778 A1 * 5/2015 Lowe ..................... A61B 6/032 378/37
2016/0228079 A1 * 8/2016 Stearns ................ A61B 5/0073
2016/0249872 A1 * 9/2016 Grass ..................... A61B 6/482 378/16
2017/0168171 A1 * 6/2017 Fung ......................... G01T 7/00
2017/0209110 A1 * 7/2017 Kiraly ...................... A61B 6/44
2017/0219498 A1 * 8/2017 Chtcheprov .......... G01T 1/2978
2017/0309063 A1 * 10/2017 Wang .................... G06T 19/003
2017/0336706 A1 * 11/2017 Wang ................... A61B 5/0071
2018/0140197 A1 * 5/2018 Wang ................... A61B 5/0077
2018/0228010 A1 * 8/2018 Butani ................... A61B 6/107
2018/0262743 A1 * 9/2018 Casas ..................... A61B 34/10
2018/0275076 A1 * 9/2018 Butani ................. A61B 6/4208
2019/0053771 A1 * 2/2019 Butani ................... A61B 6/502
2019/0059914 A1 * 2/2019 Nguyen ............... A61B 6/4482
2019/0239831 A1 * 8/2019 Chopra .................. A61B 5/065
2019/0269376 A1 * 9/2019 Butani ................... A61B 6/025
2019/0323966 A1 * 10/2019 Wang ................. G01N 21/6458
2020/0107794 A1 * 4/2020 Mandelkern ............ G06T 7/136
2020/0182807 A1 * 6/2020 Butani ............. G01N 23/20025
2020/0340931 A1 * 10/2020 Butani ............... G01N 21/6456
2020/0372644 A1 * 11/2020 Butani ................... G16H 30/20
2021/0073999 A1 * 3/2021 Atria .......................... G06T 7/11
2021/0077050 A1 * 3/2021 Chang .................... G16H 30/40
2021/0093417 A1 * 4/2021 Liu ........................ A61B 90/37
2021/0113146 A1 * 4/2021 Pogue .................... H04N 19/96
2021/0164922 A1 * 6/2021 Butani ............... G01N 21/6456
2021/0199603 A1 * 7/2021 Butani ................. G01N 23/046
2022/0304645 A1 * 9/2022 DeLong Samalik .. G16H 40/67
2022/0386968 A1 * 12/2022 Bleas ..................... A61B 6/102
2023/0011644 A1 * 1/2023 Zhao .................... A61B 6/5282
2023/0169649 A1 * 6/2023 Rao ....................... G06T 7/0012 378/62
2023/0190383 A1 * 6/2023 Krull .................... A61B 6/4411 378/163
2023/0218251 A1 * 7/2023 Hansroul ............... A61B 6/547 378/4
2023/0288182 A1 * 9/2023 Sakuma ............... G03H 1/0486
2023/0390587 A1 * 12/2023 Wong ................... A61N 5/1077
2023/0404499 A1 * 12/2023 DeFreitas ............ A61B 6/4435
2024/0398359 A1 * 12/2024 Beister ................... A61B 6/025

OTHER PUBLICATIONS

International Search Report from the International Searching Authority issued Feb. 24, 2025 for application PCT/US2024/059211 (Year: 2025).*

United States Patent and Trademark Office, International Search Report, Application No. PCT/ US2024/059211, mailed Feb. 24, 2025, 2 pages.

United States Patent and Trademark Office, Written Opinion of the International Searching Authority, Application No. PCT/US2024/ 059211, Feb. 24, 2025, 7 pages.

* cited by examiner

SYSTEM AND METHOD FOR CABINET X-RAY SYSTEMS WITH 3-D OPTICAL IMAGING RECONSTRUCTION

DIAGRAMS

FRONT VIEW INTO CABINET
Door Open

Typical Example of an X-ray Irradiator Cabinet System

SYSTEM AND METHOD FOR CABINET X-RAY SYSTEMS WITH 3-D OPTICAL IMAGING RECONSTRUCTION

CROSS-REFERENCE TO RELATED APPLICATIONS

This application is related to the following applications filed on 9 Dec. 2023, the disclosures of which are each, individually, incorporated herein by reference in their entireties: U.S. Ser. Nos. 18/534,584; 18/534,586; 18/534,587; 18/534,588; 18/534,589; 18/534,590 and 18/534,591.

BACKGROUND

Field of the Present Disclosure

The aspects of the disclosed embodiments relate to the field of a cabinet x-ray incorporating a system and method for incorporating an x-ray system and an optical camera, either high definition or standard resolution, taking a real-time image concurrently with the x-ray image/procedure, then displaying and reconstructing the resulting optical mage/s on the system monitor in 3-Dimensions.

Optical imaging is a powerful tool in biology and the medical field. Optical imaging uses a multi-frequency detector equipped with either a white beam or multi frequency light source to permit the acquisition of images at very low intensity level in a wide wavelength range. Optical imaging as incorporated in a cabinet radiography system allows better orientation and truths to the user. Among the disadvantages of optical methods are the strong scattering and absorption effects in tissue and complexity of light transport, resulting in the absence of a practical, high-resolution 3D image reconstruction algorithm. Here we propose a 3D reconstruction system and method for imaging samples that may be organic or inorganic imaged in a cabinet radiography system. We believe our approach is original one and different from other proposed approaches.

Background

Specimen Radiography is considered the most cost-effective screening method for the detection of breast cancer in surgically removed breast tissue. However, the sensitivity of specimen radiography is often limited by the presence of overlapping dense fibroglandular tissue in the breast specimen. Dense parenchyma reduces the conspicuity of abnormalities and thus constitutes one of the main causes of missed breast cancer diagnosis. The advent of full-field digital detectors offers opportunities to develop advanced techniques for improved imaging of dense breasts, such as digital tomosynthesis.

The photo/captured real-time image may be displayed on the monitor either overlaid onto the resultant x-ray image of the sample or as a Picture-In-a-Picture (PIP) adjacent to the x-ray image of the sample.

Today, conventional breast specimen systems can gather a digital breast specimen radiogram separately. In these systems, the radiograms of a tissue or bone specimen are viewed separately for analysis.

With a unit incorporating an optical camera and a system to capture and/or reconstruct the captured image into a 3-D image, the clinician can utilize the resultant photo to expeditiously visualize the specimen excised from the patient to confirm orientation of the excised sample saving time for both the patient on the treatment table and the clinician.

It would be advantageous in breast procedure rooms to allow the medical professional to operate the cabinet x-ray unit to analyze the excised breast tissue or specimen utilizing the unit to both x-ray and capture an image of the sample for informational and/or diagnostic purposes.

Embodiments of the current disclosure may alleviate the problems discussed above and/or other problems in the art. The scope of the current disclosure, however, is defined by the attached claims, and not by the ability to solve any specific problem.

Currently it is believed that there is not a system or method incorporating a real-time camera that can convert or interpret the captured 2-D images into a 3-D image in a cabinet x-ray system.

SUMMARY

In general, this disclosure may enable a device (cabinet x-ray system) utilizing a computer to capture a real-time image of the sample being x-rayed with exact orientation of the 2 images. While cameras incorporated into x-ray cabinets have been around, the particular feature differentiating this invention from previous public domain features is the differentiating factor of attaining the 2 images, X-ray and Optical, in the same and exact orientation and displaying them either PIP or overlaid upon each other.

A device capturing both an x-ray image and a real-time image of the specimen facilitates confirmation and orientation for the clinician to verify margins are achieved by the professional to the patient.

In one embodiment, the system would incorporate a laser or multi-frequency lights to modulate densities and the computer interpreting and/or constructing a 3-dimensional model of the specimen.

A preferred embodiment system would incorporate an HD (High-Definition) Camera into a cabinet x-ray unit allowing the system to capture an HD Image and x-ray image of the specimen.

The embodiment as related above explains how the aspects of the disclosed embodiments would relate to specimen radiography but the aspects of the disclosed embodiments are not isolated to specimen radiography but may be utilized for non-destructive testing, pathology as well as any radiographic analysis, organic and non-organic, requiring a cabinet x-ray system but is not limited to just an HD camera but any camera fitting within the confines of the cabinet x-ray system.

The aspects of the disclosed embodiments relate to systems, methods, and devices useful for the field of cabinet x-ray incorporating an x-ray tube, an x-ray detector, and a real-time camera for the production of organic and non-organic images. The computing device receives video data from the real-time camera and the x-ray detector and determines, based on the video data, an overlay of the captured x-ray image with the captured real-time image or display an adjacent image i.e. Picture-In-Picture (PIP). In particular, the aspects of the disclosed embodiments relate to a system and method with corresponding apparatus for taking a real-time image concurrently with the x-ray image/procedure, then displaying and reconstructing the resulting optical mage/s on the system monitor in 3-D.

In some embodiments, a scanner is disclosed. The scanner may include a camera coupled to a moving arm. The camera may be configured to move along the rail in a first direction, and the rail may be configured to move with the cart in a second direction different from the first direction. The scanner may also include an imaging device coupled to the cart.

The imaging device may be configured to capture a three-dimensional image of a subject. The subject may be an organic or in-organic specimen that fits within the x-ray cabinet, for example.

In some embodiments, a method of operating a scanner including one or more cameras configured to capture a three-dimensional image of a subject is disclosed. The method may include activating the one or more cameras. The one or more cameras may be coupled to a carriage coupled to an arm. The method may also include moving the carriage along the arm in a first direction, and moving the arm with the carriage in a second direction different from the first direction. In at least some embodiments of the current disclosure, the first direction may be transverse, e.g., substantially perpendicular, to the second direction.

Additionally or alternatively, embodiments of the method may include one or more of the following aspects: the computer system may be further configured to convert the constructed three-dimensional image of the specimen to a modified three-dimensional image, the modified three-dimensional image may be indicative of an expected outcome of a surgical procedure of the excised tissue; the computer system may include a display device to present the constructed three-dimensional image and the modified three-dimensional image; the modified three-dimensional image may represent the expected outcome of a procedure on the excised tissue; the computer system may be configured to receive input from a user and control the first motor and the second motor based on the input; the computer system may be configured to control the first motor and the second motor to move the one or more cameras in a substantially rectangular path; the computer system may be further configured to rotate the one or more cameras about at least one of a first axis extending in the first direction or a second axis extending in the second direction; the computer system may be configured to rotate the one or more cameras about the second axis while the one or more cameras are moving in the first direction.

BRIEF DESCRIPTION OF THE DRAWINGS

To further clarify the above and other advantages and features of the present invention, a more particular description of the invention will be rendered by reference to specific embodiments thereof that are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION

Figure 1:
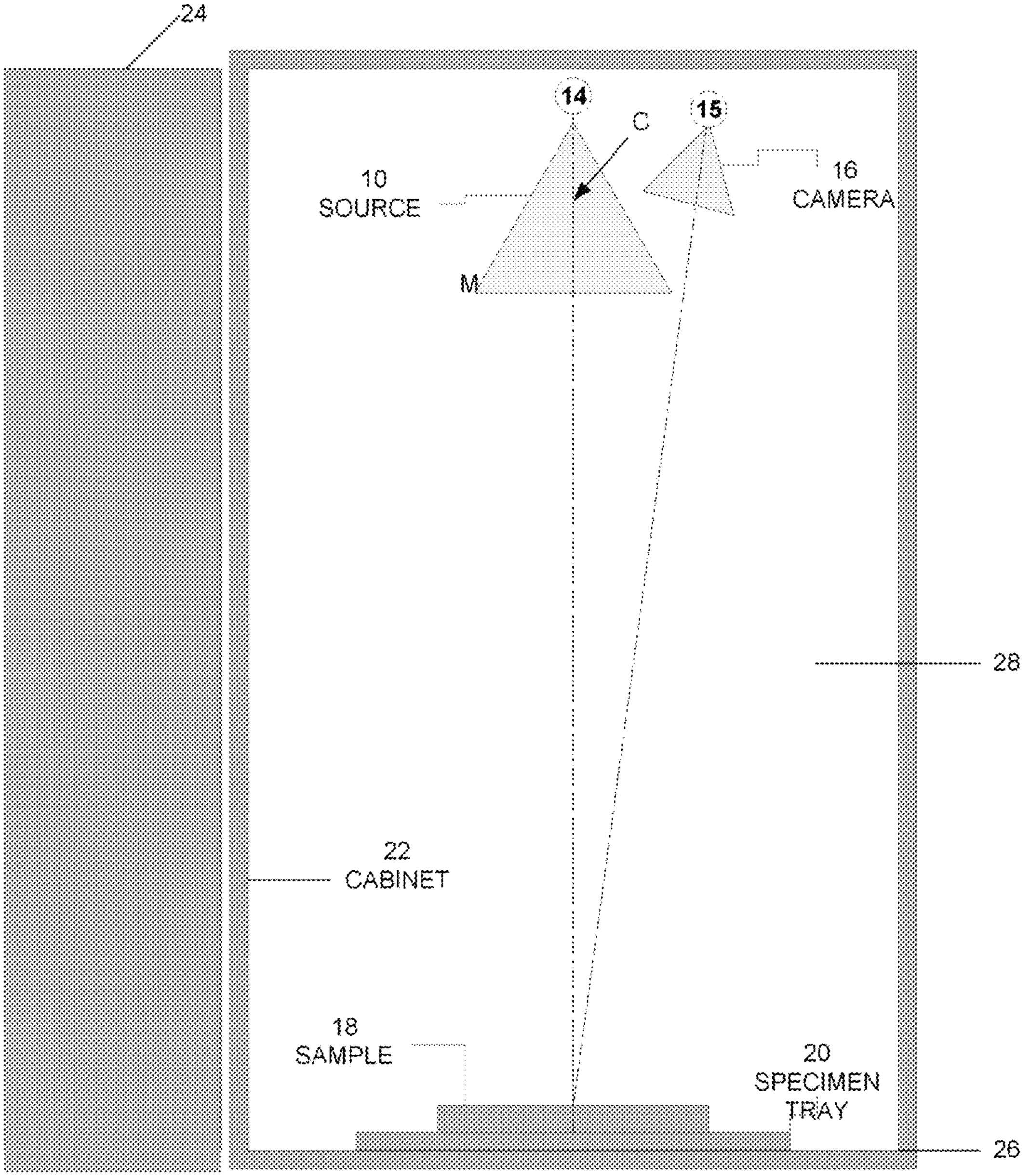
FIG. 1 is one example embodiment of the aspects of the disclosed embodiments.
Figure 2:
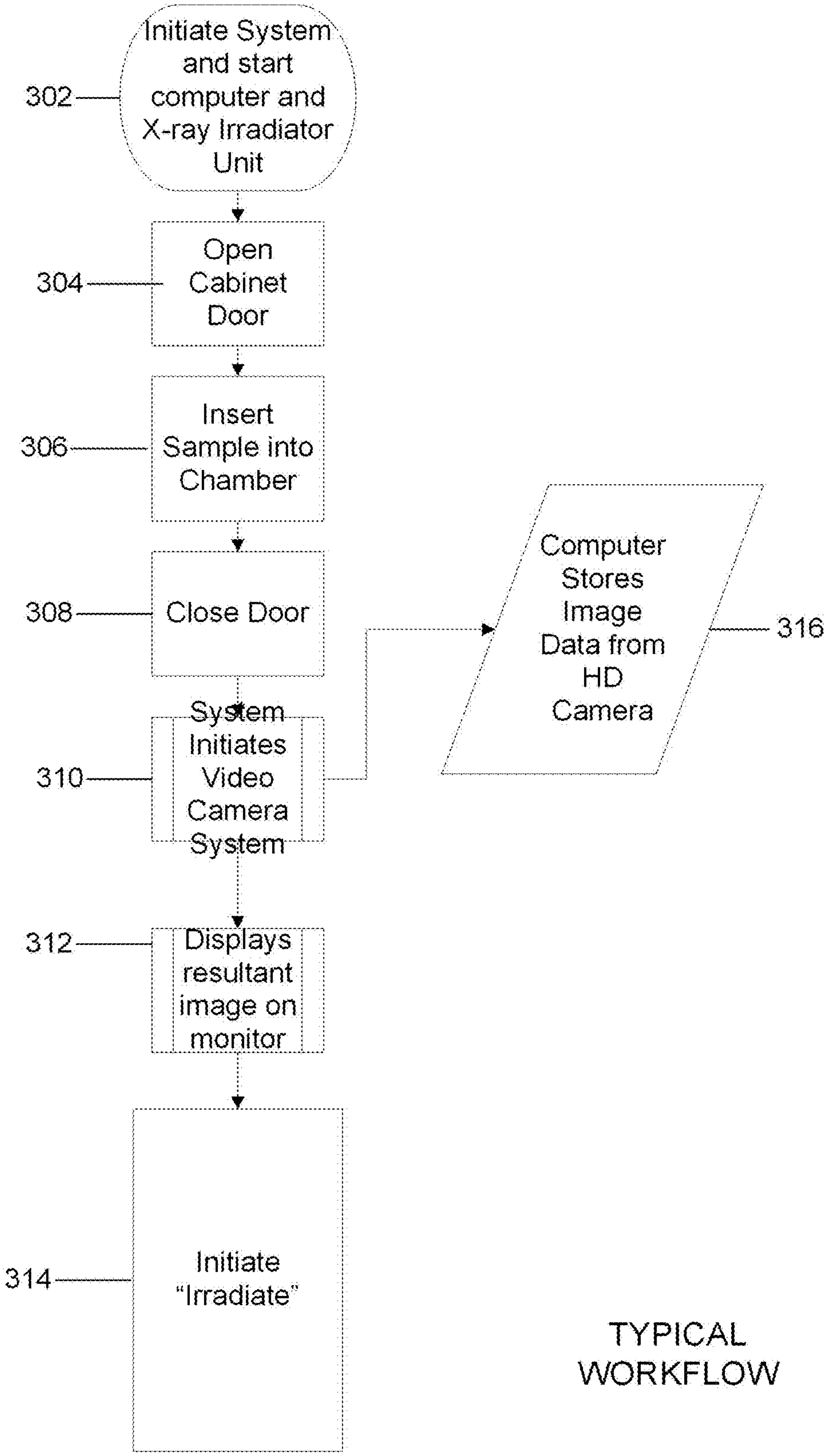
FIG. 2 is a display of the basic workflow of the one example embodiment.
Figure 3:
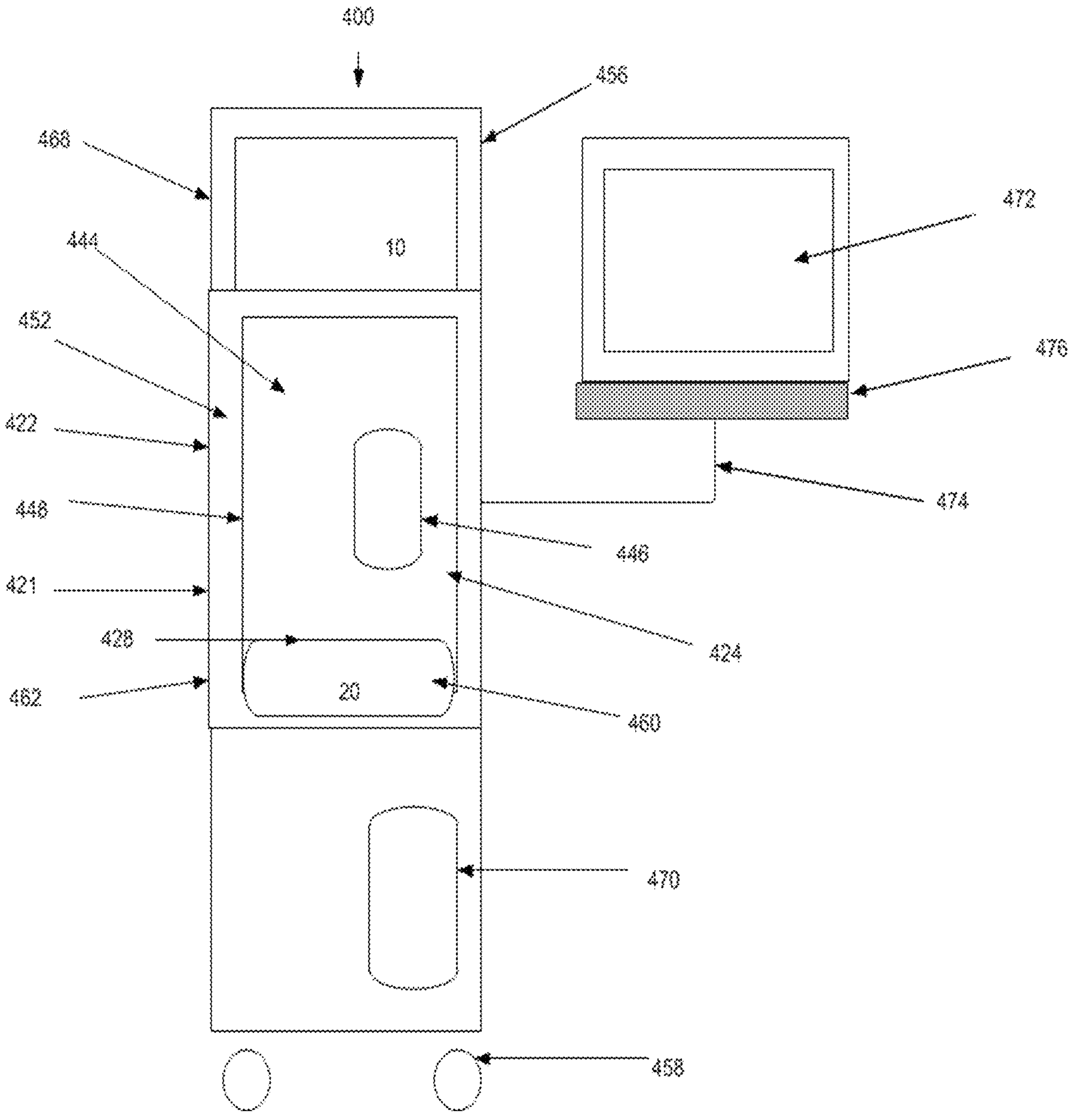
FIG. 3 is view in the sample chamber of the example embodiment of the present disclosure.

Reference will now be made to figures wherein like structures will be provided with like reference designations. It is understood that the drawings are diagrammatic and schematic representations of exemplary embodiments of the invention, and are not limiting of the present invention nor are they necessarily drawn to scale. FIGS. 1-3 depict various features of embodiments of the present invention, which embodiments are generally directed to a system that can utilize a real-time camera to capture an image of the specimen/sample concurrently with the acquisition of an x-ray image.

Referring first to FIG. 1, there is shown an example of the embodiment of a camera incorporated into a Cabinet X-Ray Unit. The medical professional or other authorized operator places a specimen/sample into the chamber, closes and secures the door, and presses acquire on the computer screen. Simultaneously the computer commands the camera, x-ray source in conjunction with the x-ray detector to capture images and display them either overlaid or adjacent PIP (Picture-in-Picture) on the monitor. This, in turn, provides more flexibility for a clinician or other user of the system and simplifies the procedure. Manual input for operation of the cabinet x-ray unit may be initiated via keyboard and the resulting image from both the manual-initiated examination is displayed on the screen and configured in accordance with one example embodiment of the present disclosure.

Figure 4:
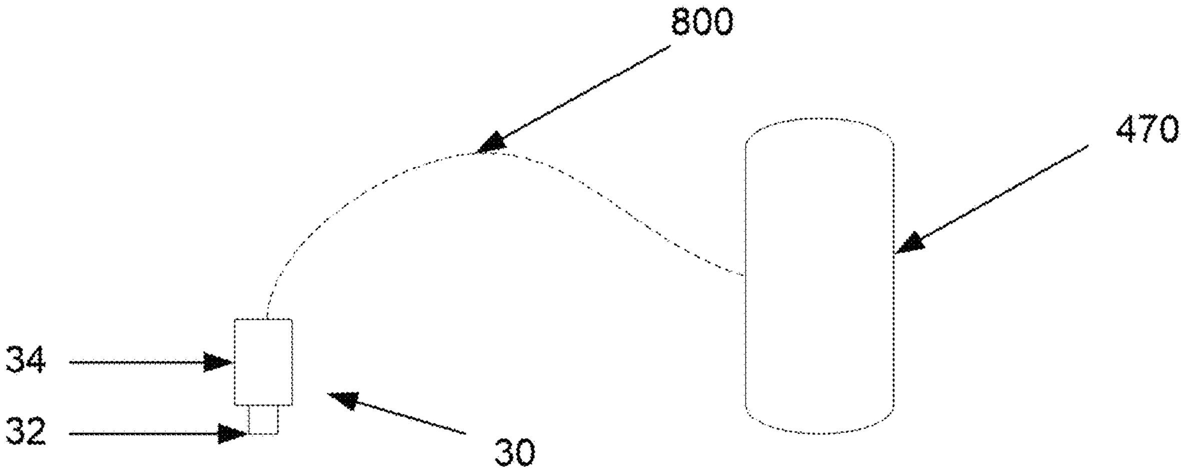
FIG. 4 displays an imaging system incorporating aspects of the disclosed embodiments.

FIG. 2 displays the basic workflow of the cabinet x-ray unit. FIG. 3 displays the front view into the cabinet x-ray unit. FIG. 4 displays a camera system.

Currently it is believed that there is not a system or method incorporating a real-time camera in a cabinet x-ray system with exact orientation of the 2 images nor able to reconstruct a 3-dimensional image.

Indeed, it is appreciated that the system and its individual components can include additional features and components, though not disclosed herein, while still preserving the principles of the present invention. Note also that the base computer can be one of any number devices, including a desktop or laptop computer, etc.

The aspects of the disclosed embodiments may be embodied in other specific forms without departing from its spirit or essential characteristics. The described embodiments are to be considered in all respects only as illustrative, not restrictive. All changes that come within the meaning and range of equivalency of the claims are to be embraced within their scope.

What is claimed is:

1. A cabinet x-ray system incorporating a real-time camera, comprising:
- a computer;
- a base unit including an image processor and a display;
- an imaging chain incorporated into the base unit, including:
  - an x-ray source with an x-ray detector;
  - a scanner including the real time camera configured to capture a three dimensional image of a specimen concurrently with an acquisition of an x-ray image, wherein the computer is configured to:
    - control a first motor and a second motor to move the real-time camera in a substantially rectangular path;
    - rotate the camera about at least one of a first axis extending in a first direction or a second axis extending in a second direction; and
    - rotate the camera about the second axis while the camera is moving in the first direction;
  - an interface for enabling a signal to be transferred from the real-time camera to the computer, and
  - a laser for constructing a 3-dimensional model of the specimen for which the three dimensional image and x-ray image are acquired.

2. The system as defined in claim 1, in which the real-time camera is configured to supply standard or High-Definition (HD) real-time images.

3. The system of claim 1, in which the cabinet x-ray system concurrently captures an x-ray image and a real-time image.

4. The system of claim 1, in which the real-time camera is mounted onto the system such that the x-ray image and real-time image are captured at a specific orientation.

5. The system of claim 1, in which the base unit is enclosed in the cabinet x-ray system.

6. The system of claim 1, in which the base unit is utilized for excised tissue, organ or bone specimens.

7. The system of claim 1, in which the base unit is utilized for any specimen that fits inside the x-ray cabinet.

8. The system of claim 1 in which the scanner is mounted in the cabinet x-ray system.

9. The system of claim 1 in which the real-time image is displayed overlaid onto the x-ray image or adjacent to the x-ray image.

10. The system of claim 1 in which the imaging chain is composed of sources emitting at differing frequencies.

* * * * *